United States Patent [19]
West et al.

[11] Patent Number: 5,756,047
[45] Date of Patent: May 26, 1998

[54] AIR PURIFICATION METHOD

[75] Inventors: Donald E. West, Los Gatos; Richard E. Wickham, Soquel, both of Calif.

[73] Assignee: Advanced Chemical Systems, Inc., Milpitas, Calif.

[21] Appl. No.: 572,328

[22] Filed: Dec. 14, 1995

Related U.S. Application Data

[63] Continuation-in-part of Ser. No. 372,281, Jan. 13, 1995, abandoned, which is a continuation-in-part of Ser. No. 102,100, Aug. 4, 1993, Pat. No. 5,397,546.

[51] Int. Cl.$^6$ ............................................. A01N 59/12
[52] U.S. Cl. ........................ 422/37; 422/124; 422/125; 95/212; 95/224; 95/225
[58] Field of Search ................... 422/37, 123, 124, 422/125, 178; 55/222, 233, 257.2, 242; 95/212, 224, 225; 261/DIG. 46

[56] References Cited

U.S. PATENT DOCUMENTS

| | | | |
|---|---|---|---|
| 3,547,576 | 12/1970 | Sheikh | 21/53 |
| 3,857,677 | 12/1974 | Moore et al. | 21/58 |
| 3,926,802 | 12/1975 | Hedgpeth | 210/59 |
| 3,969,479 | 7/1976 | Lonnes et al. | 423/210 |
| 4,045,192 | 8/1977 | Eckstein et al. | 55/222 |
| 4,061,570 | 12/1977 | Fletcher et al. | 210/96 M |
| 4,200,442 | 4/1980 | Willot | 55/222 |
| 4,261,837 | 4/1981 | West et al. | 210/754 |
| 4,343,765 | 8/1982 | Elston et al. | 422/3 |
| 4,367,149 | 1/1983 | Kinman | 210/753 |
| 4,670,223 | 6/1987 | Delachapelle | 422/122 |
| 4,775,484 | 10/1988 | Schmidt et al. | 210/673 |
| 4,784,835 | 11/1988 | Fritz | 422/170 |
| 4,844,874 | 7/1989 | deVries | 423/210 |
| 4,888,118 | 12/1989 | Barnes et al. | 210/668 |
| 4,935,064 | 6/1990 | Robbins et al. | 134/2 |
| 5,017,351 | 5/1991 | Ratson | 423/245.2 |
| 5,104,527 | 4/1992 | Clinkenbeard | 210/94 |
| 5,126,044 | 6/1992 | Magnusson et al. | 210/282 |
| 5,176,836 | 1/1993 | Sauer et al. | 210/670 |
| 5,273,687 | 12/1993 | Osborne | 261/29 |
| 5,389,120 | 2/1995 | Sewell et al. | 55/223 |
| 5,397,546 | 3/1995 | West et al. | 422/37 |
| 5,531,800 | 7/1996 | Sewell et al. | 55/223 |
| 5,531,801 | 7/1996 | Sewell et al. | 55/223 |

*Primary Examiner*—Nina Bhat
*Attorney, Agent, or Firm*—David H. Jaffer

[57] ABSTRACT

Scrubber sterilization method which initially sterilize a gas scrubber with an initial cleaning with hydrogen peroxide, provide an iodine level of approximately 5 to 10 mg/liter in water which is sprayed into the scrubber to contact the effluent gas stream and kill biological growth, provide injection of more concentrated iodine in water in the event the iodine level in the system falls below a predetermined level, and load the filtrate material in the gas scrubber with iodine to provide an unfavorable surface for adherence of biological growth as well as a secondary sterilization means in the event that the liquid stream with iodine is stopped due to equipment or power failure.

10 Claims, 5 Drawing Sheets

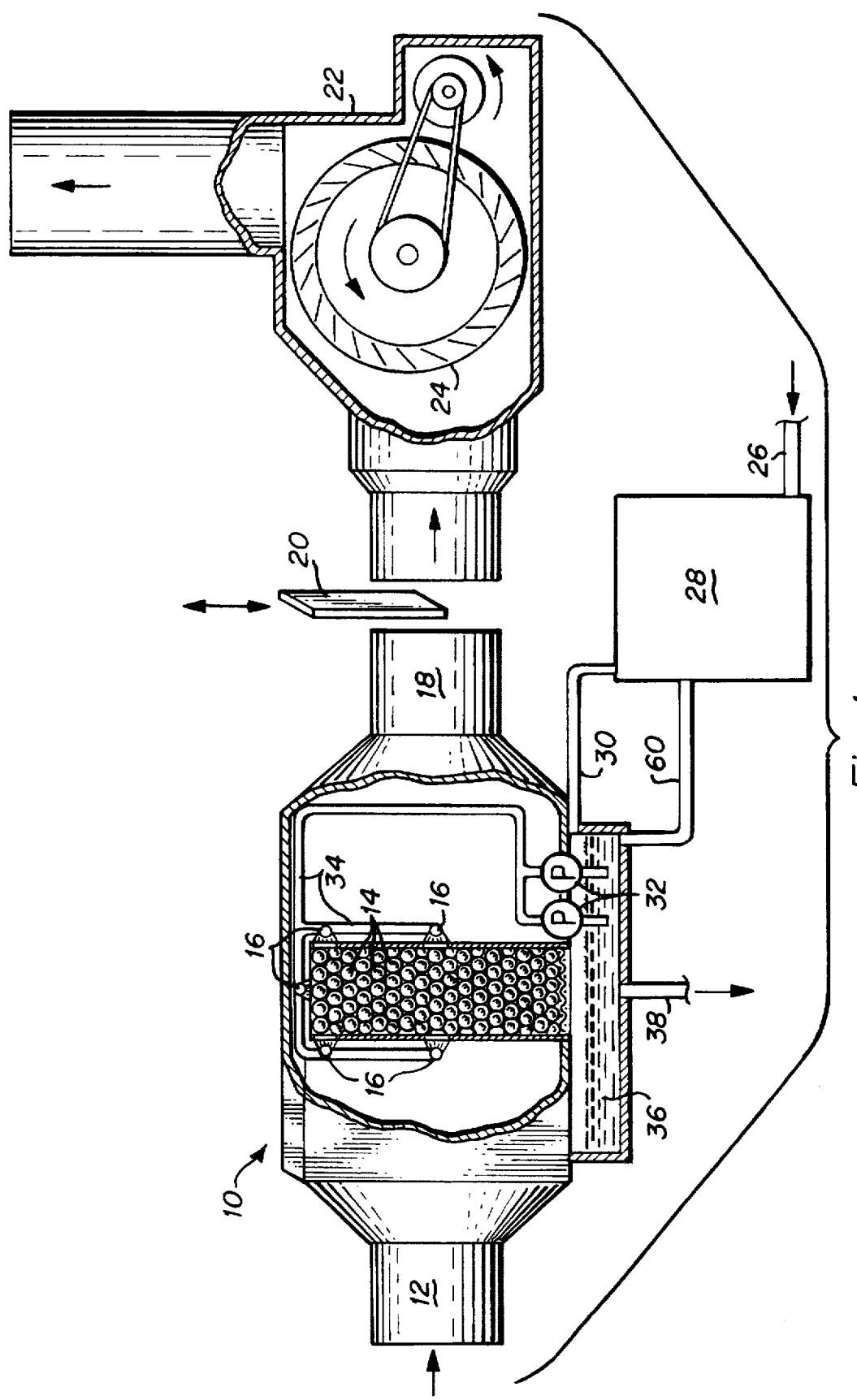
Fig_1

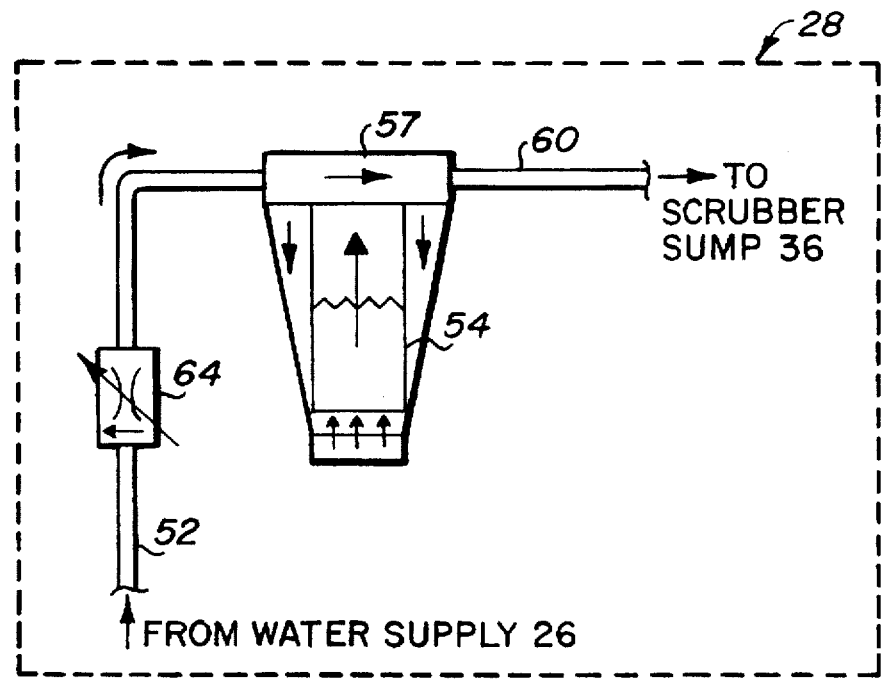
Fig_2A
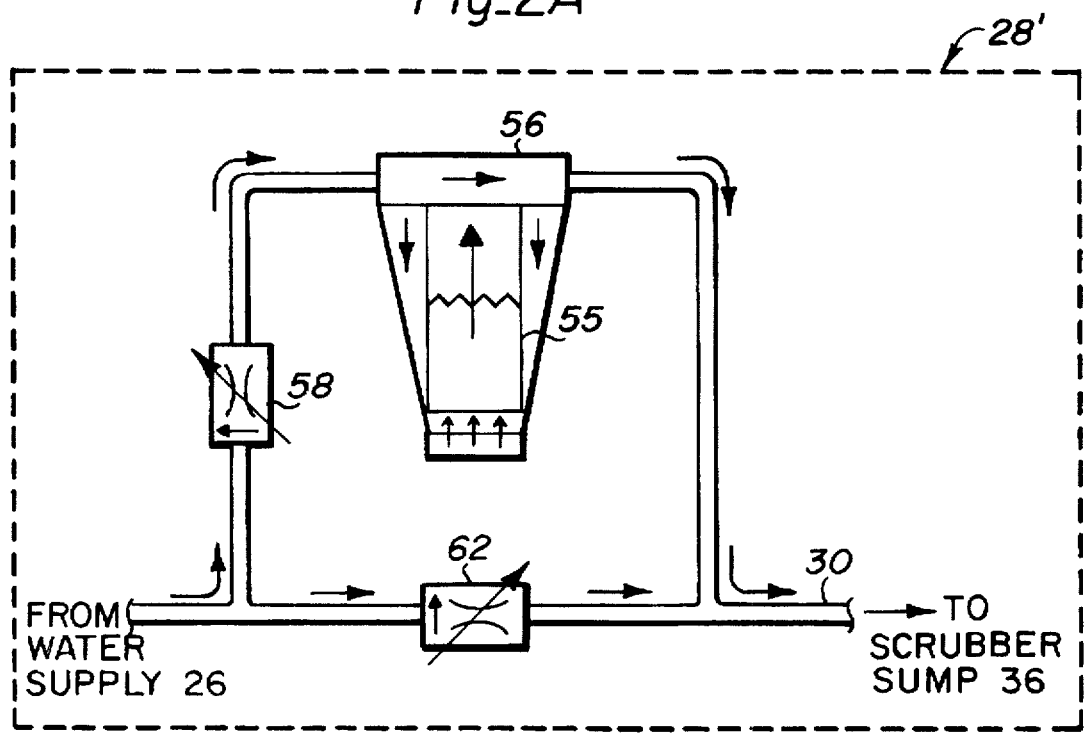
Fig_2B

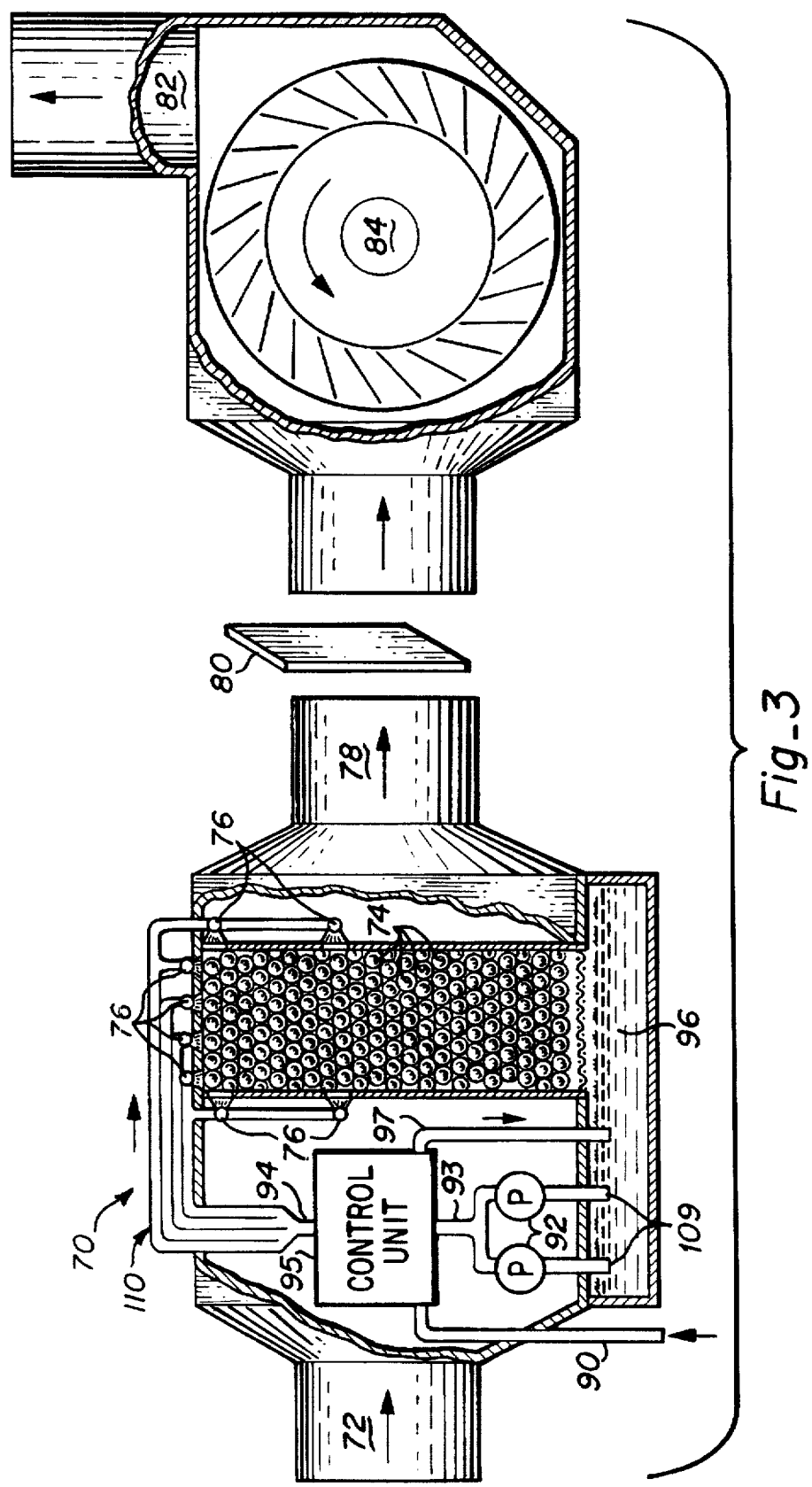

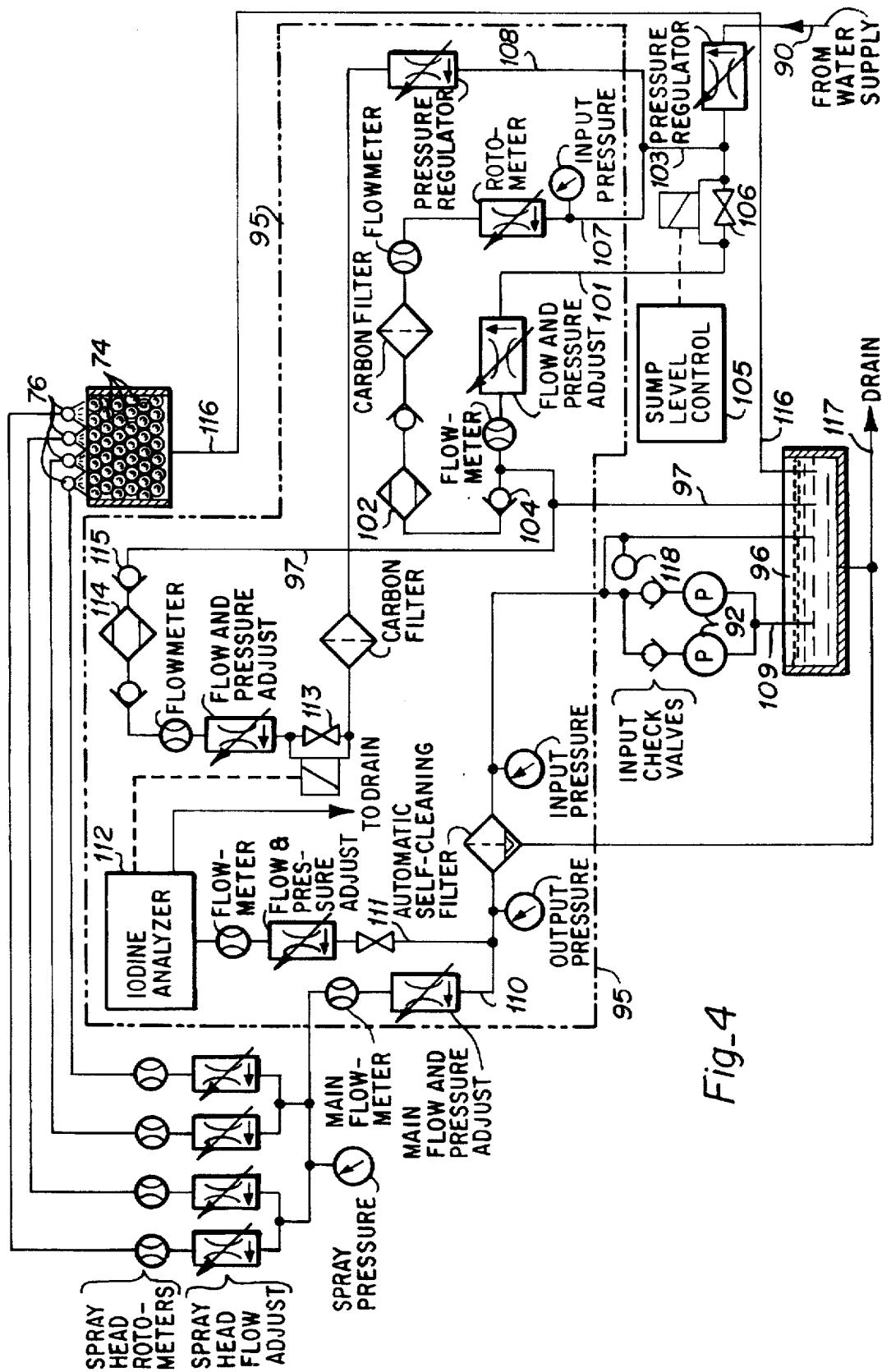
Fig_4

AIR PURIFICATION METHOD

This application is a continuation-in-part of 08/372,281 filed Jan. 13, 1995, now abandoned which is a continuation-in-part of 08/102,100 filed Aug. 4, 1993, now U.S. Pat. No. 5,397,546.

BACKGROUND OF THE INVENTION

1. Field of the Invention

The present invention relates generally to a method and apparatus for controlling biological growth in gas scrubber systems. In particular, this invention relates to a method and apparatus which utilize a mixture of iodine in water to control biological growth, thereby eliminating or greatly reducing the need to shut down the gas scrubber for periodic cleaning and permitting the scrubber to be used continuously.

2. Brief Description of the Prior Art

Gas and acid fume scrubbers are widely used to eliminate odorous or hazardous constituents from gas streams. Scrubbers are used in many applications, including smoke emitted from burning of fuels, effluent gas streams from chemical processing (including acid fumes), and sewage treatment. The gas stream to be scrubbed, which may also contain solid particulate and/or liquid droplets of contaminants, is contacted with a liquid (usually water) which may contain reagents that react with the unwanted constituents in a gas stream, thereby condensing and/or neutralizing the unwanted constituents. The scrubbing may occur in a bed packed with a solid having a large surface area, thereby increasing the surface area at which the liquid and the gas may contact each other, as shown in Lonnes et al., U.S. Pat. No. 3,969,479; in a reaction chamber in which a mist of the liquid contacts the gas, as shown in deVries, U.S. Pat. No. 4,844,874; or in filters, as shown in Fritz, U.S. Pat. No. 4,784,835.

Gas scrubbers are prone to biological growth which inhibits gas flow, causes contamination of the process with which the gas scrubber is associated (which may be of particular importance in applications requiring high cleanliness, such as electronics and semiconductor processing), and causes clogging of the packing material or filter, as well as clogging of the spray jets which are used to provide the liquid to the packing material, filter, or mist reactor. Such contamination has been removed in the past by shutting down the gas scrubber, and sterilizing the scrubber with cleaning materials such as bleach or hydrogen peroxide. These cleaning procedures are by their nature repetitive, since biological growth begins again immediately, and costly because the process associated with the scrubber must be stopped until the scrubber has been cleaned and put back on line.

Iodine has been known for some time to be an effective means of purifying water. See U.S. Pat. Nos. 5,176,836; 5,126,044; 4,935,064; 4,888,118; 4,367,149; and 4,261,837. In addition, iodine has been used in air deodorizing and disinfecting, as shown in Elston et al., U.S. Pat. No. 4,343,765 and Sheikh, U.S. Pat. No. 3,547,576.

SUMMARY OF THE INVENTION

It is a primary object of the present invention to provide a method and an apparatus to control biological growth, including bacteria, yeast, viruses, fungi, protozoa, and algae in a gas scrubber system.

It is a further object of the present invention to provide a method and an apparatus for sterilization of a gas scrubber system, whereby biological growth in the system is removed in a pre-treatment step and thereafter controlled so that the gas scrubber is continuously kept clean and may be operated continuously without periodic shutdown for repeated removal of accumulated biological growth.

It is still another object of the present invention to provide a method and apparatus for an air purification system, whereby bacterial and other biological growth in the system is removed in a pre-treatment step and thereafter controlled so that the air purification system continuously purifies and is kept clean allowing for continuous operation of the system without periodic shutdown for repeated removal of accumulated biological growth.

Another object of the present invention is to provide a secondary sterilization method which is operable in the event that a gas scrubber is shut down through equipment or power failure.

A further object of the present invention is to provide a method and an apparatus which safely and economically control biological growth in a gas scrubber system, thereby eliminating or greatly reducing the need for periodic shutdown of the gas scrubber for sterilization and eliminating or greatly reducing the risk involved in cleaning of the gas scrubber.

Briefly, the preferred embodiment of the present invention is a method and an apparatus which initially sterilize a gas scrubber with an initial cleaning with hydrogen peroxide, provide an iodine level of approximately 0.5 to 10 mg/liter in water which is sprayed into the scrubber to contact the effluent gas stream and kill biological growth, provide injection of more concentrated iodine in water in the event the iodine level in the system falls below a predetermined level, and load the filtrate material in the gas scrubber with iodine to provide an unfavorable surface for adherence of biological growth as well as a secondary sterilization means in the event that the liquid stream with iodine is stopped due to equipment or power failure.

BRIEF DESCRIPTION OF THE DRAWINGS

FIG. 1 is a plan view of a scrubber system in accordance with the present invention;

FIG. 2A & B are a schematic views of the iodination apparatus used with the system shown in FIG. 1;

FIG. 3 is a plan view of an alternative embodiment of the scrubber system;

FIG. 4 is a detailed view of the iodination unit used in the system shown in FIG. 3

DESCRIPTION OF THE PREFERRED EMBODIMENT

Figure 5:
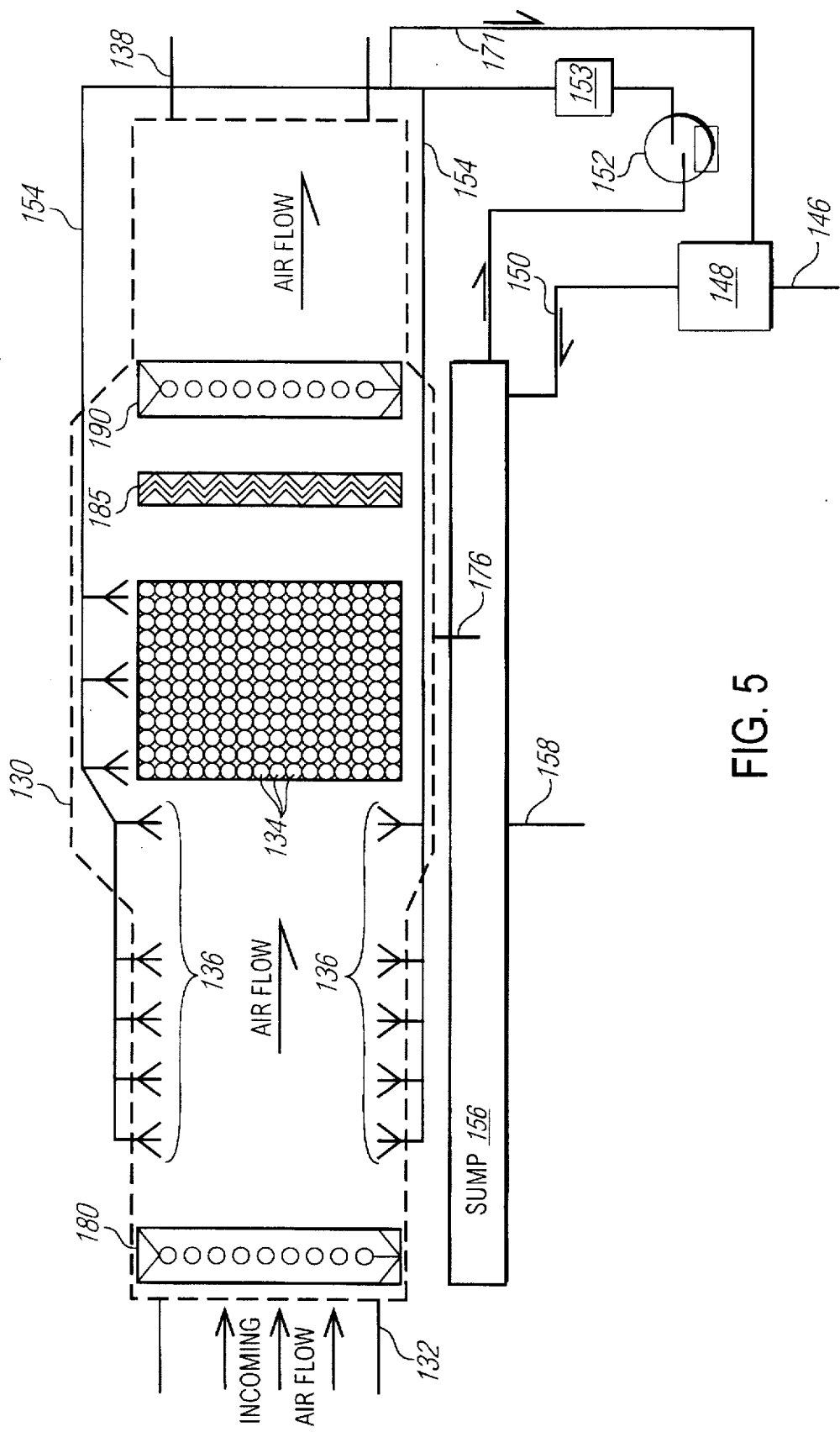
FIG. 5 is a plan view of an alternative embodiment of the scrubber system.

This invention provides a method and an apparatus which effectively reduce biological growth in a gas or acid fume scrubber, thereby improving the effectiveness of the scrubber, reducing or eliminating downtime and costs associated with downtime, and reducing maintenance costs. The invention is suitable for use in scrubbers for cleaning hazardous or odorous gas streams, and also for maintaining sterilization of gas scrubbers as may be used for cleaning air in buildings (for example, recirculating heating and air conditioning systems).

With reference to FIG. 1, a scrubber sterilization system in accordance with the present invention is shown. Fume scrubber 10 includes gas intake vent 12, which receives exhaust gas from the source or process which generates the unwanted or contaminated gas emissions. Fume scrubber 10 includes a filtrate packing section including a solid material with high surface area. In a preferred embodiment of the invention, this packing material is comprised of polypropylene filtrate packing balls 14. The balls are formed to have increased surface area, for example with an open fence-type mesh, rather than having a solid spherical exterior surface. The balls used in this embodiment are approximately 4 inches in diameter, with a number of separate bands of polypropylene of approximately 1/8 inch width defining the perimeter of the sphere (the bands separated to permit gas and liquid flow) and with internal bands of similar width adding further surface area and structural support. Alternatively, the filtrate packing section can utilize another nonreactive solid material, such as other forms of plastic, glass, etc. Alternatively, a filter comprised of numerous fibers would also serve as an acceptable solid material with high surface area.

As in the prior art, spray nozzle heads 16 spray a liquid, preferably water in this preferred embodiment, over the filtrate packing, wetting the filtrate packing and providing a large surface area in which the effluent gas may contact the liquid. As in the prior art, this wetting of the effluent gas scrubs unwanted constituents of the gas stream from the gas stream by condensing them or reacting with them. The clean scrubbed gas exits the scrubber through gas output vent 18. The flow of gas through the fume scrubber 10 is controlled with control damper 20, allowing adjustment of the flow rates, thereby regulating the time which the effluent gas stream contacts the liquid in the filtrate packing. Beyond the fume scrubber 10 is exhaust piping 22 for the cleaned scrubbed gas. A variable speed fan 24 allows further control of the rate of flow of the effluent gas through fume scrubber 10, and also provides a pressure differential which serves to pull the effluent gas through the fume scrubber.

The present invention controls biological growth in the filtrate packing through the addition of trace iodine to the liquid stream, preferably water, that is used to wet the filtrate packing balls 14. Water is supplied to the apparatus through water supply pipe 26 which provides water to an iodination system 28, where elemental iodine is added to the water supply in the amount of about 0.5 to 10 mg/liter, preferably 5 to 10 mg/liter. Once the water has been iodinated, water is input to the fume scrubber sump 36 through pipe 30 or pipe 60. Recirculation pumps 32 pump water from sump 36 through piping 34 to spray heads 16, which spray the iodinated water onto the filtrate packing 14. Contaminated sump water can be drained to waste treatment facilities through water output pipe 38.

In an example of the present invention, fume scrubber 10 is used to scrub effluent gas from a semiconductor processing and fabrication operation. The filtrate packing section is approximately 9 feet×9 feet×2 feet, and filled with polypropylene filtrate packing balls 14. The overall dimensions of the fume scrubber are approximately 12 feet×9 feet×9 feet. The exhaust piping 22 is approximately 4 feet in diameter, and utilizes a variable speed fan capable of pulling 30,000 to 50,000 cubic feet per minute. The liquid flow through spray heads 16 is approximately 18,000 gallons per hour of water. This water recirculates through pumps 32. Approximately 2,000 to 6,000 gallons of fresh water per day are added as water vapor is drawn off in the exhaust piping or through water output pipe 38.

As FIG. 1 indicates, in the preferred embodiment, iodine is added to the water by two methods. These methods are shown in more detail in FIG. 2, which is a schematic drawing of iodination system 28. FIG. 2(b) illustrates the method used to iodinate all of the make-up water added to sump 36. Incoming water flows through water supply pipe 26 through piping to iodination cartridge 55. Cartridge 55 contains elemental iodine and the rate of water entering cartridge 55 is sufficient to add the desired amount of concentrated iodine to the water stream 30 in pipe 30 to maintain the iodine concentration in sump 36 at the desired level. Cartridge 55 preferably is a canister-like container that holds about one gallon of water and nine pounds of iodine. The cartridge 55 is fitted into place in the piping by rotating it into a threaded fitting 56. Control of the incoming water to cartridge 55 for iodine injection into the make-up water stream is controlled by rotometer 58. Control of the make-up water volume is controlled by rotometer 62. Relatively high concentration iodine solution is produced in the cartridge 55 and is diluted in a larger volume of incoming water flowing through rotometer 62 to produce a lower concentration in the make-up water (10–60 mg/liter). The water may also be buffered to maintain a desired pH range in scrubber sump 36.

In addition to iodinating the incoming water for the scrubber sump, we have found it to be advantageous to control the iodine concentration in the sump in some cases. This control is required in order to respond to sudden and variable changes in the iodine concentration of the recirculated sump water. Such changes result from fluctuations in the flux of materials passing through the scrubber. For example, there may be a sudden flux of acid, biological material, or other hazardous, odorous, or contaminated material in the gas stream passing through the scrubber.

The methodology for control of iodine concentration in the recirculated sump water is based upon continuous sampling of the sump water recirculation system. The sample is automatically tested for iodine concentration. Set points allow for automatic switching of a solenoid controlling water flow through an iodine cartridge canister. When a low iodine concentration is reached, the low level alarm signal commands the system to allow a saturated stream of iodinated water to be injected into the scrubber sump. Once a sufficiently high level of iodine concentration is reached, a high level alarm signal commands shutoff of the flow of saturated iodinated water to the scrubber sump.

FIG. 2(a) represents the means through which more highly concentrated iodine is injected into the sump in response to a command for iodine to be added to the sump water from a halogen analyzer which indicates that the level of iodine has fallen below a threshold level. Incoming water flows through water supply pipe 52 (which is taken off water supply pipe 26) and through iodination cartridge 54. Cartridge 54 contains elemental iodine and the rate of water entering cartridge 54 is sufficient to add the necessary amount of concentrated iodine to sump 36 through pipe 60. Cartridge 54 is a canister-like container that holds about one gallon of water and about nine pounds of iodine, and is fitted into connection 57 by rotating it into a threaded fitting. Control of the incoming water to cartridge 54 for iodine injection into sump 36 is controlled by rotometer 64.

A cumulative water meter (not shown) may be provided to allow the user knowledge of the amount of water that has been iodinated, thereby allowing the user to determine when the cartridge/canister needs replacing. A carbon bed and filter (not shown) may be installed prior to the iodination cartridges, ensuring that the feeder system will not be contaminated or clogged up by contaminants from the water source. Metering valves, flowmeters, and check valves provide control of iodine concentration and flow rates.

In accordance with the present invention, the scrubber is initially sterilized to remove as much biological matter as possible. This process involves shutdown of the gas scrubber. The filtrate packing is removed and sterilized. The inside of the scrubber is cleaned, for example with a high-pressure peroxide washdown using 8% to 30% hydrogen peroxide in water.

During this high-pressure washdown, the filtrate packing balls 14 are removed and cleaned. The filtrate packing balls are then treated with an aqueous solution of 100–300 mg iodine per liter of water. We have found that the iodine becomes loaded from the aqueous solution onto the polypropylene filtrate packing balls 14 when the water is free of biological matter. This loading of the filtrate packing balls 14 with iodine provides a secondary source of iodine in the event that the gas scrubber is shut down and the iodinated water flow from the spray heads is not available. As long as the water circulated through the spray heads is relatively free of biological matter, the iodine on the filtrate packing balls 14 remains on the filtrate packing balls, because the affinity of iodine for the polypropylene filtrate packing balls is greater than the affinity of iodine to the water. However, if biological growth begins in the water surrounding the filtrate packing, as would happen if the water from the spray heads stopped or if the iodination of the water circulating through the spray heads was insufficient, biological growth would begin. In that event, we have found that the affinity of iodine is greater for the water containing the biological growth than is the affinity of the iodine for the polypropylene filtrate packing balls. Therefore, by loading iodine onto the filtrate packing material, we provide a secondary method for maintaining the sterilization of the scrubber system.

After the filtrate packing section has been sterilized with a high-pressure peroxide washdown and the polypropylene filtrate balls have been loaded with iodine, the filtrate packing area is reloaded with filtrate packing balls 14. The incoming water from water supply 26 is iodinated in iodination system 28 and the iodinated water is pumped to spray heads 16 from sump 36 by recirculation pumps 32 through piping 34. Since the system has been sterilized during the initial steps, only a relatively low level of iodine in the water provided to the filtrate packing balls through the spray heads is required to prevent or sharply reduce biological growth.

With reference to FIG. 3, an alternative embodiment of the scrubber system which utilizes a subsystem for controlling iodine concentration in the recirculated sump water is shown. Scrubber 70 includes gas intake vent 72, which receives exhaust gas from the source or process which generates the unwanted or contaminated gas emissions. Scrubber 70 includes a filtrate packing section including a solid material with high surface area, as discussed with reference to FIG. 1. The packing material is shown as packing balls 74. Spray nozzle heads 76 spray a liquid, preferably water, over the filtrate packing, wetting the filtrate packing, and providing a surface area in which the effluent gas may contact the liquid. The clean scrubbed gas exits the scrubber through gas output vent 78. The flow of gas through scrubber 70 is controlled with control damper 80, allowing adjustment of the flow rates. Beyond scrubber 70 is exhaust piping 82 for the clean scrubbed gas. Variable speed fan 84 allows further control of the rate of flow of the effluent gas through scrubber 70.

Water is supplied to the apparatus through water supply pipe 90. Pipe 90 connects to iodination monitoring and control unit 95, which is described below in detail with reference to FIG. 4. Iodinated water leaving iodination unit 95 is distributed through piping 110 to spray heads 76, which spray the iodinated water onto filtrate packing 74. Water passing over filtrate packing 74 drains to sump 96. Water from sump 96 is pumped by recirculation pumps 92 back through piping 93 to iodination unit 95, for recirculation through spray heads 76.

With reference to FIG. 4, a detailed drawing of iodination monitoring and control unit 95 and its relationship to the scrubber is shown. Iodination unit 95 includes the elements encompassed by the dotted line in FIG. 4, with other elements of the scrubber shown outside of the dotted line. Water supply pipe 90 provides fresh water into the system. This flow is divided into pipes 101 and 103. Pipe 101 provides make-up water to the sump when the total volume of water in the sump falls below a pre-set level. Sump level control 105 monitors the level of water in sump 96, and when the level falls below a preset level, make-up injection solenoid 106 opens a valve to provide additional water to sump 96 through pipe 97. Pumps 92 lift water through pipe 109 from sump 96, passing it through input check valves and pressure gauges through an automatic self-cleaning filter. The major part of the water lifted by pumps 92 passes through pipe 110 through pressure adjustment valves and flowmeters to spray heads 76, where the water passes over filtrate packing 74, draining to sump 96 by drip drain path 116.

In this embodiment, iodination unit 95 first injects iodinated water to the make-up water for sump 96 with base concentration of iodine (5–60 mg/liter) in water, monitors the amount of iodine in the sump water, and provides a second iodination injection system which can provide a larger volume of iodine directly to sump 96 in the event that the level of iodine in the recirculating sump water falls below a pre-set limit, as may happen if there is a sudden flux of material which consumes the iodine added through the first iodine injection method.

The level of iodine in the sump water is continuously or periodically monitored by obtaining a sample of the water from sump 96 through pipe 111 and providing it to iodine analyzer 112. Iodine analyzer 112 monitors the level of iodine in the water using an automated calorimeter.

The base level of iodine in the sump water provided to the spray heads 76 is added to the fresh water input through pipe 107 by iodination cartridge 102 and iodine injector 104. The second level of control of iodine concentration in the sump water is provided by halogen analyzer 112, which directly monitors the water in sump 96. Pipe 108 provides water to iodination cartridge 114, where a saturated solution of iodine in water is created (approximately 300 mg/liter). When halogen analyzer 112 detects that the iodine concentration has fallen below a pre-set level it activates injection solenoid 113 to open iodine injector 115. Iodine injector 115 injects this saturated iodine in water solution directly into sump 96 through pipe 97 until the desired iodine concentration is reached. In the preferred embodiment, the iodination cartridge shown in 114 is preferably one gallon of water with about nine pounds of iodine, as is iodination cartridge 102. Drain line 117 is provided to extract waste water from sump 96 and filtered waste water from the automatic self-cleaning filter.

The system also uses pH monitor 118 to monitor the pH in sump 96. If an undesirable pH is reached, a signal is sent to dump sump water and replace it with iodinated make-up water.

An alternative embodiment of this invention utilizes a method and apparatus similar to that described above for an air purification system. This embodiment is appropriate for use in an air purification system where a sterile environment is preferred and bacterial or other biological contaminants can accumulate and/or grow.

With reference to FIG. 5, an air purification system in accordance with the present embodiment is shown. Purifier 130 includes air intake vent 132, which receives air to be purified. Purifier 130 includes a first heat exchanger 180 for optimizing the temperature of the incoming air by either heating or cooling. Optimal temperature is dependent on the air to be purified and is normally in the range of between 10° C. and 40° C. The air then passes through a series of spray heads 136 which saturate the air with a liquid, preferably water. Saturation of the air lengthens the air to liquid contact time. The saturated air then passes through a filtrate packing section including a solid material with high surface area, as discussed with reference to FIG. 1. The packing material is shown as packing balls 134. Spray nozzle heads 136 also spray a liquid, preferably water, over the filtrate packing wetting the filtrate packing, and providing a surface area in which the air may contact the liquid. The purified air then passes through mist eliminator 185 which removes mist and water droplets from the air. The removed water from the mist eliminator drains to sump 156 by drip drain path 176. The de-misted air then enters a second heat exchanger 190 to dehumidify the purified air which then exits the system through air output vent 138. The flow of air through air purifier 130 is controlled by a damper or other volume adjusting device positioned after air output 138.

As described above, biological growth in the filtrate packing section and elimination of biological contaminants in the air is controlled through the addition of trace iodine to the liquid stream which is used to wet filtrate packing balls 134. Water is supplied to the system through water supply pipe 146 which provides water to iodination system 148. Iodination system 148 is discussed above with reference to FIGS. 2(a) and 2(b). Once iodinated, the water is directed to sump 156 through pipe 150. Recirculation pump 152 then pumps water from sump 156 through piping 154 to spray heads 136, which spray the iodinated water onto the filtrate packing 134. Filter 153 removes dead biological material, however, contaminated sump water can be drained to waste treatment facilities through water output pipe 158.

In accordance with the present embodiment, the purifier may be initially sterilized to remove any accumulated biological matter present in the system. This process is described above with reference to FIG. 1.

As indicated in FIG. 5, in the preferred embodiment, iodine is added to the water via pipe 150. There are two methods for introducing iodine to the water which are discussed above with reference to FIGS. 2(a) and 2(b). A sample of the water is continually supplied to iodination unit 148 through sample pipe 171 for monitor and control of the concentration of iodine in the recirculated water.

This invention, involving the method and apparatus described above, may be applied to any recirculating or closed loop water system where a sterile condition is preferred and bacterial or other biological contaminants can accumulate and/or grow. It also is applicable to any water system where biological control is required or monitoring and iodination techniques can be applied. More specifically, these applications include systems involving air preparation (e.g. temperature and/or humidity control), cooling towers, scrubbers (particulate or gas fume), deionized water recirculating closed loop systems, and air strippers for evaporating VOC's out of soil.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method for air purification comprising the steps of:
   (a) providing an air purification system including an air intake vent, a first heat exchanger, a filtrate section having filtrate material and means for wetting the filtrate material, a mist eliminator, a second heat exchanger, and an air output vent, whereby a flow of air to be purified enters the air purification system through the air intake vent, flows past the first heat exchanger, flows through the filtrate section, flows through the mist eliminator, flows past the second heat exchanger, and exits through the air output vent; and
   (b) during operation of the air purification system, wetting the filtrate material with water containing iodine at a frequency, duration and iodine concentration sufficient to purify the air and to control biological growth on the filtrate material, wherein the water containing iodine is provided to the means for wetting the filtrate material of the air purification system from an iodination system in which iodine is added to water by flow of a stream of water through a cartridge containing elemental iodine.

2. The method of claim 1, wherein the iodine concentration is in the range of 0.5 to 10 mg of iodine per liter of water.

3. The method of claim 1, further comprising the step of pre-treating the filtrate material with an aqueous iodine solution having a higher concentration of iodine than the solution of iodine in water used to wet the filtrate material.

4. The method of claim 3, wherein the iodine concentration in the filtrate wetting solution is in the range of 0.5 to 10 mg of iodine per liter of water.

5. The method of claim 4, wherein the iodine concentration in the pre-treatment solution is in the range of 100 to 300 mg of iodine per liter of water.

6. The method of claim 3, wherein the iodine concentration in the pre-treatment solution is in the range of 100 to 300 mg of iodine per liter of water.

7. A method for air purification comprising the steps of:
   (a) providing an air purification system including an air intake vent, a first heat exchanger, a filtrate section having filtrate material and means for wetting the filtrate material, a mist eliminator, a second heat exchanger, and an air output vent, whereby a flow of air to be purified enters the air purification system through the air intake vent, flows past the first heat exchanger, flows through the filtrate section, flows through the mist eliminator, flows past the second heat exchanger, and exits through the air output vent;
   (b) pre-treating the filtrate material with an aqueous iodine solution; and
   (c) wetting the filtrate material with water containing iodine at a frequency, duration, and iodine concentration sufficient to purify the air and to control biological growth on the filtrate material, wherein the water containing iodine is provided to the means for wetting the filtrate material of the air purification system from an iodination system in which iodine is added to water by flow of a stream of water through a cartridge containing elemental iodine, and wherein the pre-treating iodine solution has a higher concentration of iodine than the solution of iodine in the water used to wet the filtrate material.

8. The method of claim 7, wherein the iodine concentration in the filtrate wetting solution is in the range of 0.5 to 10 mg of iodine per liter of water.

9. The method of claim 8, wherein the iodine concentration in the pre-treatment solution is in the range of 100 to 300 mg of iodine per liter of water.

10. The method of claim 7, wherein the iodine concentration in the pre-treatment solution is in the range of 100 to 300 mg of iodine per liter of water.

* * * * *